United States Patent [19]
McCombs et al.

[11] Patent Number: 5,833,704
[45] Date of Patent: Nov. 10, 1998

[54] POWERED HIGH SPEED ROTARY SURGICAL HANDPIECE CHUCK AND TOOLS THEREFORE

[75] Inventors: Daniel L. McCombs, Grand Rapids; James G. Walen, Kalamazoo, both of Mich.

[73] Assignee: Stryker Corporation, Kalamazoo, Mich.

[21] Appl. No.: 882,190

[22] Filed: Jun. 25, 1997

Related U.S. Application Data

[62] Division of Ser. No. 740,477, Oct. 30, 1996, Pat. No. 5,735,535, which is a division of Ser. No. 314,819, Sep. 29, 1994, Pat. No. 5,634,933.

[51] Int. Cl.⁶ ................................................. A61B 17/32
[52] U.S. Cl. ........................... 606/180; 408/226; 606/80
[58] Field of Search ................................. 606/108, 80, 79, 606/1, 167, 170, 171, 180, 159; 279/86, 131, 55, 57, 58, 77, 119, 123; 408/231–233

[56] References Cited

U.S. PATENT DOCUMENTS

| | | |
|---|---|---|
| D. 216,286 | 12/1969 | Valeska . |
| 234,066 | 11/1880 | Reno . |
| D. 377,982 | 2/1997 | Walen . |
| 2,609,209 | 9/1952 | Perman . |
| 3,564,948 | 2/1971 | Pomernacki . |
| 4,232,985 | 11/1980 | Nielsen . |
| 4,565,472 | 1/1986 | Brennsteiner et al. . |
| 5,011,408 | 4/1991 | Nakanishi . |
| 5,167,476 | 12/1992 | Lafferty et al. . |
| 5,403,134 | 4/1995 | Andersson et al. . |
| 5,601,560 | 2/1997 | Del Rio et al. . |
| 5,630,818 | 5/1997 | Del Rio et al. .......................... 606/180 |
| 5,634,933 | 6/1997 | McCombs et al. ...................... 606/180 |
| 5,735,535 | 4/1998 | McCombs et al. ...................... 606/180 |

FOREIGN PATENT DOCUMENTS

| | | |
|---|---|---|
| 1 007 851 | 3/1983 | U.S.S.R. . |
| 1 053 978 | 11/1983 | U.S.S.R. . |

OTHER PUBLICATIONS

Photocopy of a cross sectional view of a prior high speed rotational surgical handpiece including a chuck of the kind used with below discussed p. 14, Figure 20 tool shank A.
Photocopy of brochure No. 1000–33 REV Jul. 1994 entitled Command 2 Oral and Maxillofacial, pp. 1–4.
"Command2 MicroElectric System" Maintenance Manual & Operating Instructions: Photocopy of p. 14, Figures 19 and 20 show prior art (on sale more than 1 year prior to filing date of present application) shanks A, B and C.
Sketch A (shank A pictorial view).

*Primary Examiner*—Glenn K. Dawson
*Attorney, Agent, or Firm*—Flynn, Thiel, Boutell & Tanis, P.C.

[57] ABSTRACT

A replaceable rotary patient tissue working tool and a high speed rotational surgical handpiece having a centrifugal chuck for axial push-in chucking and pull-out release of such a tool includes a chuck including a centrifugal locking member with a mass portion located on one side of a rotational axis of a drive shaft. The centrifugal locking member is pivoted on an axis transverse to the drive shaft axis and has a leg extending past said rotational axis. The leg has tool gripping structure on the opposite side of such rotational axis for receiving a tool rear shank rearward axially therepast and for more strongly radially gripping such a tool shank in response to faster rotation of the drive shaft. The invention, in another aspect, includes a tool having an elongate shank, patient tissue working structure at a front end of the shank and mounting structure at the rear end of the shank. The mounting structure includes a radially depressed plateau engageable by such centrifugal locking member.

4 Claims, 5 Drawing Sheets

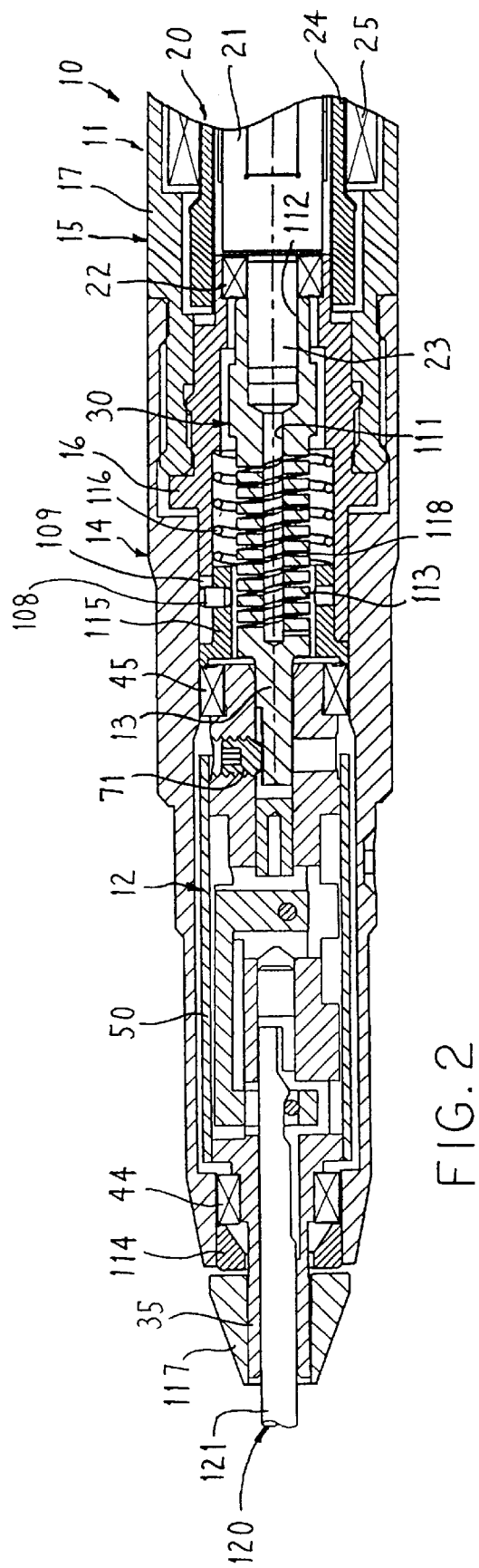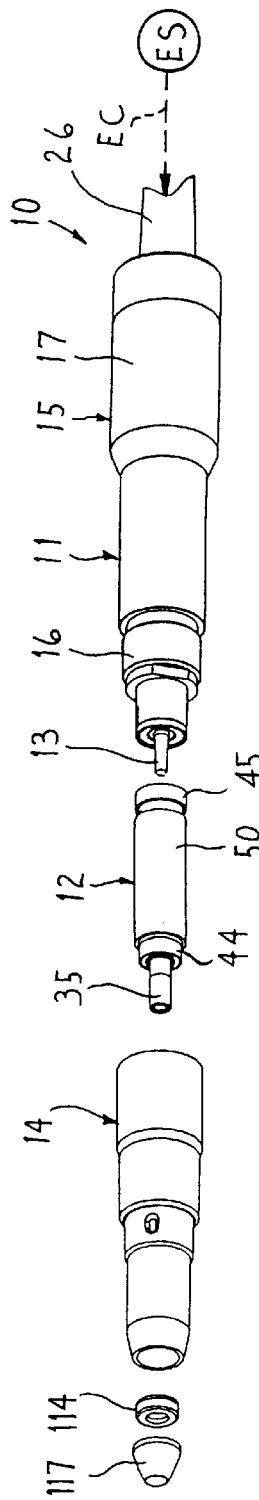
FIG. 2
FIG. 1

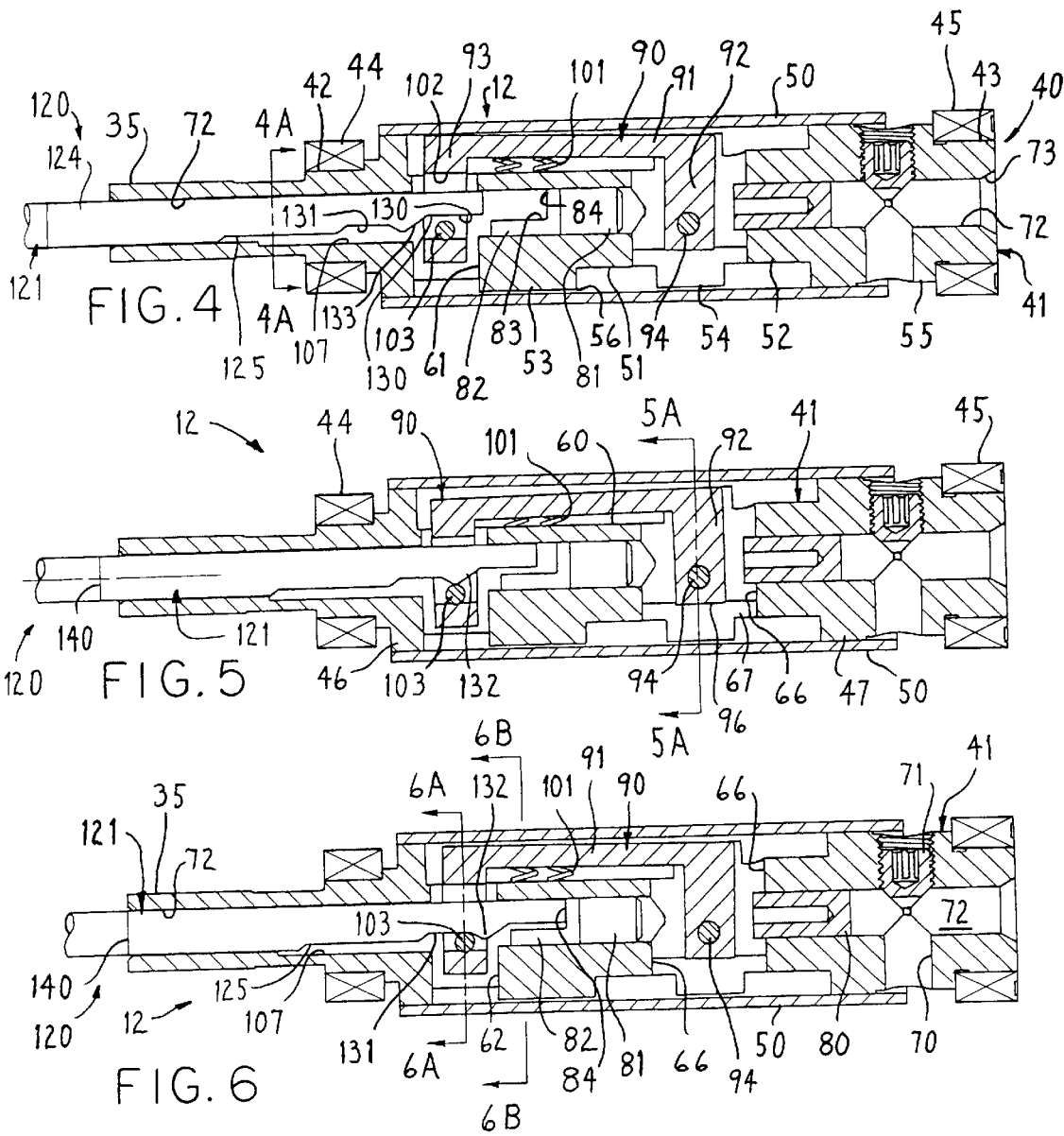

POWERED HIGH SPEED ROTARY SURGICAL HANDPIECE CHUCK AND TOOLS THEREFORE

This is a division of Ser. No. 08/740,477, filed Oct. 30, 1996, now U.S. Pat. No. 5,735,535, which is a division of Ser. No. 08/314 819, now U.S. Pat. No. 5,634,933.

FIELD OF THE INVENTION

This invention relates to a powered, high speed, rotary surgical handpiece chuck and tools therefore.

BACKGROUND OF THE INVENTION

The assignee of the present invention has for a number of years marketed high speed rotary handpieces, for example under the model designation 100K, and more recently 100 K2 (a 100,000 rpm handpiece). While these prior art handpieces (which include prior art chucks), and chuckable tools to be used therewith, have worked well and been commercially successful, the present invention was developed in a continuing effort to improve on apparatus of this general type.

SUMMARY OF THE INVENTION

A replaceable rotary patient tissue working tool and a high speed rotational surgical handpiece having a centrifugal chuck for axial push-in chucking and pull-out release of such a tool comprises a chuck including a centrifugal locking member with a mass portion located on one side of a rotational axis of a drive shaft. The centrifugal locking member is pivoted on an axis transverse to the drive shaft axis and has a leg extending past said rotational axis. The leg has tool gripping structure on the opposite side of such rotational axis for receiving a tool rear shank rearward axially therepast and for more strongly radially gripping such a tool shank in response to faster rotation of the drive shaft. The invention, in another aspect, includes a tool having an elongate shank, patient tissue working structure at a front end of the shank and mounting structure at the rear end of the shank. The mounting structure includes a radially depressed plateau engageable by such centrifugal locking member.

Further objects and purposes of the present invention will be apparent to persons acquainted with apparatus of this general type upon reading the following description and reviewing the accompanying drawings.

BRIEF DESCRIPTION OF THE DRAWINGS

FIG. 1 is an exploded pictorial view of a high speed rotary surgical handpiece including a chuck embodying the invention.

FIG. 2 is an enlarged fragmentary cross sectional view of the FIG. 1 handpiece, showing the chuck and rotary drive embodying the invention.

FIG. 4 is an enlarged central cross sectional view of the FIG. 1 chuck with a removable tool, embodying the invention, at a first stage of insertion into the FIG. 1 chuck.

FIG. 5 is a view similar to FIG. 4 with the tool in a second stage of insertion into the chuck.

FIG. 6 is a view similar to FIG. 4 but with the tool fully inserted into the chuck.

DETAILED DESCRIPTION

Figure 3:
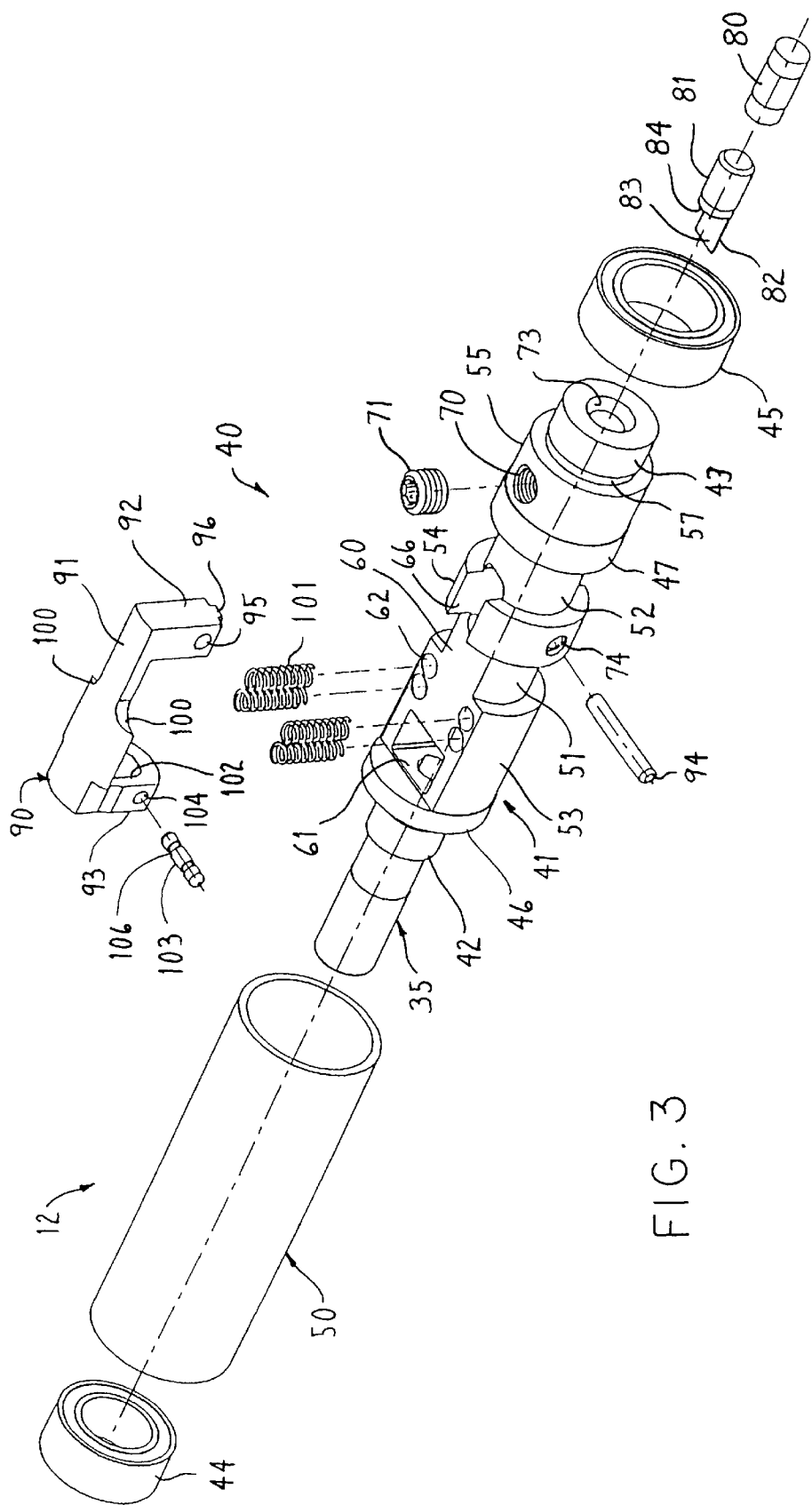
FIG. 3 is an exploded pictorial view of the FIG. 1 chuck embodying the invention.

A high speed rotary surgical handpiece 10 (FIG. 1) comprises a motor assembly 11 and a chuck 12 rotatably driven by a rotatable shaft 13 extending forward coaxially from the motor assembly 11. The chuck 12 is housed in a chuck housing 14 fixed on the front of a motor housing 15 of the motor assembly 11. The motor assembly 11 may be of any convenient type capable of driving the rotary shaft 13 at high rotational speeds. In handpieces of this general type, rotary shaft speeds of for example, 85,000 rpm and 100,000 rpm are known. The motor housing 15 here comprises an annular front part 16 fixedly telescoped, as seen in FIG. 2, in an annular rear part 17.

In the embodiment shown, the motor assembly 11 includes a conventional electrically powered motor generally indicated at 20 (FIG. 2) and comprising an elongate rotor 21 rotationally supported by bearings (the front one of which is shown at 22 in FIG. 2) and having a forward extending, reduced diameter motor shaft 23 rotatably supported by such front bearing 22. The front bearing 22 in turn is supported fixedly within the rear end portion of the front part 16 of the motor housing 15. The motor 20 further includes an annular winding 24 surrounding the rotor 21 in clearance relation and fixed on the rear end portion of the motor housing front part 16, the winding 24 in turn carrying surrounding laminations of magnetic material 25. The rear part 17 (FIG. 1) of the motor housing 15 supports and surrounds the windings 24 and laminations 25 and extends to the rear end of the handpiece 10 which includes a suitable rear bearing not shown but typically similar to the front bearing 22. A sheath 26 (FIG. 1) carries electrical conductors, schematically indicated in broken line at EC, connected to a suitable electric power source ES.

An axially elongate coupler 30 is fixed at its rear end, by any conventional means not shown, coaxially on the motor shaft 23 and extends coaxially forward therefrom. The front end of the coupler 30 coaxially fixedly carries the rotary shaft 13, which in turn is coaxially received in and fixed to and rotatably drives the chuck 12. The chuck 12, which rotates with the rotatable shaft 13, in turn carries a forward protruding hollow coaxial extension 35, which opens forward to receive a tool removably therein for rotation thereby.

To the extent above described, the apparatus of FIGS. 1 and 2 is conventional and may, for example, be of the kind marketed by the present assignee, Stryker Corporation of Kalamazoo, Mich., under the model numbers 296-100 and 2296-100 and names 100K and 100K II, respectively.

Attention is now directed to portions of the disclosed apparatus more particularly involving the present invention.

The inventive chuck 12 (FIG. 3) includes a rotatable drive shaft 40 comprising an elongate generally cylindrical body 41 and the hollow extension 35. The rear end of the body 41 is rotatably driveable by the rotatable shaft 13 of FIG. 1. The forward end of the body 41 fixedly coaxially and preferably integrally supports the forward extending, hollow rotatable extension 35. The extension 35 which is of reduced diameter compared to the average diameter of the body 41. The body 41 is generally in the form of a right circular cylinder except as noted hereafter.

Reduced diameter, cylindrical bearing support portions 42 and 43 are provided at the front and rear ends of the body 41. The bearing support portions 42 and 43 have high speed, low friction bearings (for example, high speed ball bearings) 44 and 45, respectively, fixedly surrounding the same. The outer races of the bearings 44 and 45 in turn are axially slidable within the chuck housing 14 for rotatably supporting the drive shaft 40 within the chuck housing 14.

The chuck body 41 further includes axially short, generally cylindrical, front and rear, annular, shell 50 supporting ribs 46 and 47 (FIG. 3). The ribs 46 and 47 represent the maximum diameter of the body 41 and are of identical diameter. The front and rear ribs 46 and 47 are axially spaced from each other. The front rib 46 is immediately behind the front bearing support 42 and the rear rib 47 is spaced ahead of the rear bearing support 43 by a portion hereafter described. The ribs 46 and 47 fixedly support and are snugly surrounded by front and rear portions, respectively, of a rigid tubular sleeve 50. The sleeve 50 covers most of the axial length of the body 41, as seen in FIG. 5, by extending from near the front bearing 44 to near the rear bearing 45. The sleeve 50 is fixed on the ribs 46 and 47 by any conventional means, such as a shrink fit, adhesive bonding, or the like, to provide a liquid tight seal therewith.

Two relatively deep, generally rectangular cross section grooves 51 and 52 (FIG. 3) are incised in the body 41. The rear groove 52 is immediately ahead of the rear rib 47. The front groove 51 is spaced forward from the rear groove 52 and is spaced to a larger extent rearward from the front rib 46.

Figure 4A:
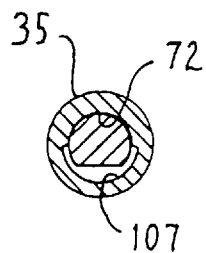
FIG. 4A is an enlarged sectional view substantially taken on the line 4A—4A of FIG. 4.

The body 41 further has front, mid and rear substantially cylindrical portions 53, 54 and 55, which are of diameter slightly smaller than the annular ribs 46 and 47. Thus, there is a small radial clearance between these substantially cylindrical portions 53, 54 and 55 and the surrounding shell 50, such clearance being generally indicated at 56 in FIG. 4. More particularly then, the front substantially cylindrical portion 53 extends axially between the front rib 46 and front groove 51, the mid substantially cylindrical portion 54 extends axially between the grooves 51 and 52 and the rear substantially cylindrical portion 55 extends rearward from the rib 47 substantially to the rear bearing support portion 43, being separated therefrom by a small relief groove 57.

A chordal flat 60 (FIGS. 3 and 5) extends rearward from the front rib 46 to the mid substantially cylindrical portion 54 as seen in FIGS. 3 and 5. The chordal flat 60 is wider along the front substantially cylindrical portion 53 and narrower along the front groove 51. The chordal flat 60 is thus deeper radially than the front groove 51. In the circumferential orientation of the body 41 shown in FIGS. 3–6, the chordal flat 60 faces upward.

The body 41 further includes a substantially rectangular hole 61 (FIGS. 3 and 4) formed by any conventional means (e.g. wire EDM'd) perpendicularly down through the chordal flat 60, axially immediately behind the forward rib 46. The rectangular hole 61 passes diametrally through the body 41 and is centered widthwise on the chordal flat 60.

Also, penetrating down into the chordal flat 60, axially between the rectangular hole 61 and the forward groove 51, are four blind holes 62 axially aligned in pairs, the two pairs being spaced chordally away from each other so that each pair lies immediately adjacent a corresponding lateral side edge of the chordal flat 60.

A further diametral hole 66 of generally rectangular shape, is formed by any conventional means (e.g. milled) down (in the orientation of the shaft in FIGS. 3–6) through the body 41 at the mid substantially cylindrical portion 60. The hole 66 is of lesser lateral width than the rectangular hole 61 but of greater axial extent, so as to extend somewhat into the portions of the annular grooves 51 and 52 flanking the mid substantially cylindrical portion 54. In the preferred embodiment shown, the bottom portion of the diametral hole 66 is of reduced lateral width (is necked in), as generally indicated at 67 in FIGS. 3 and 5A.

A further diametral hole 70 extends downward (in the circumferential orientation of the body 41 in FIGS. 3–6) through the rear substantially cylindrical portion 55. The upper portion of the diametral hole 70 is threaded to receive a set screw 71 (FIGS. 3 and 6). The hole 70 extends diametrally through the body 41 despite the fact that only the top half is threaded, because a diametral through hole is easier to tap than a blind radial hole and because the loss of material in the bottom portion of the hole 70 as seen in FIG. 6 assists in balancing of the rotating mass of the chuck. The sleeve 50 also positively precludes the set screw 71 from threading radially out of the chuck body. A locking compound is applied to the threads of the set screw 71 to maintain it in a preset radially inward, operative position radially opposing a flat on the coupling rotatable shaft 13 as hereafter more fully discussed.

As seen in FIG. 4, a central opening, or bore, 72 extends coaxially through the entire length of the body 40 and rotary extension 35. This coaxial central bore 72 thus intersects the above described rectangular diametral rectangular holes 61 and 66 and set screw hole 70. The rear end of the coaxial central bore 72 is flared, as indicated at 73 in FIG. 3.

Figure 5A:
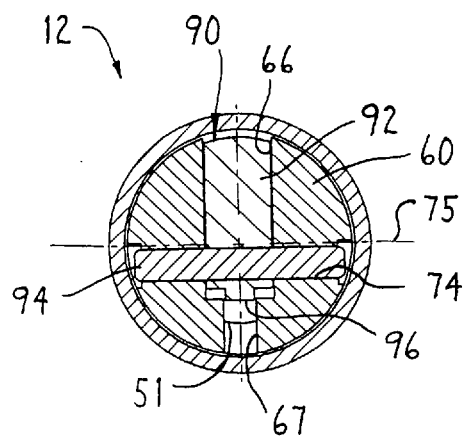
FIG. 5A is an enlarged sectional view substantially taken on the line 5A—5A of FIG. 5.
Figure 6A:
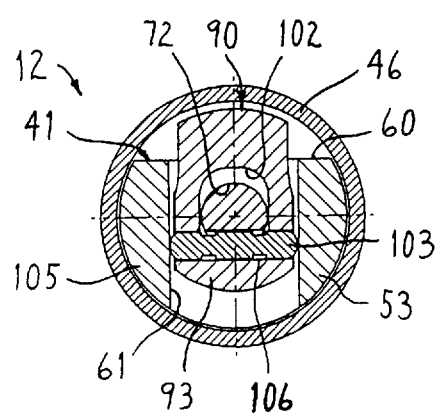
FIG. 6A is an enlarged sectional view substantially taken on the line 6A—6A of FIG. 6.
Figure 6B:
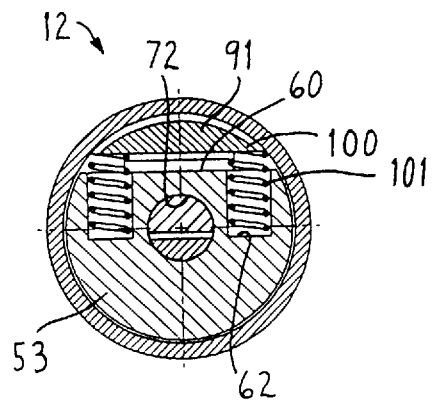
FIG. 6B is an enlarged sectional view substantially taken on the line 6B—6B of FIG. 6.

A transverse hole 74 (FIGS. 3 and 5A) extends through the mid substantially cylindrical portion 54, slightly below (in the circumferential orientation of the block in FIGS. 3–6) the body horizontal diametral plane, indicated by the chain line in FIG. 5A at 75, and thus intersects the rear rectangular hole 66.

The chuck 12 further includes a sealing plug 80 (FIGS. 3 and 6) which is fixed in and sealingly axially closes the coaxial central opening 72 in the body 41 at an axial location between the diametral through hole 66 and set screw 71. The sealing plug 80 thus lies radially inboard of the rear annular groove 52. The sealing plug 80 is fixed within the body 41 by any convenient means such as a press fit, adhesive bonding, or the like. The sealing plug 80 prevents rearward (rightward in FIG. 6) travel therepast of any liquid that might enter the front end of the central bore 72 from the surgical site, and therewith cooperates with the shell 50 for the same purpose, both ultimately preventing rearward travel of liquid from the surgical site into the chuck bearings 44 and 45.

An abutment plug 81 (FIGS. 3 and 6) is fixed snugly in the body 41 at an axial location between the rectangular diametral through holes 61 and 66. Most of the front end portion of the abutment plug 81 is removed to leave a radially and circumferentially slim, forward protruding ledge 82 which, in the circumferential orientation of the body 41 in FIGS. 3 and 6, has an upward facing chordal flat 83 and an axially rearwardly recessed forward facing abutment surface 84 (FIG. 4) for stopping rearward insertion of a tool, as hereafter discussed.

The chuck 12 further includes a rocker member 90. In the preferred embodiment shown, the rocker 90, as seen from the side in FIGS. 3–6, is of inverted, substantially U-shaped elevational profile. The rocker 90 serves as a centrifugal locking member for tools inserted in the front end of the chuck 12 as hereafter discussed. The rocker 90 has a generally axially extending bight 91, a rear leg 92 depending radially inward from the rear end of the bight 91 and a front leg 93 depending radially inward from the front end of the bight 91 (FIGS. 3 and 4).

The rear leg 92 extends down into the rear rectangular diametral through hole 66. A transverse pivot pin 94 (FIGS. 3, 5 and 5A) extends through the transverse hole 74 in the body 41 and a corresponding transverse hole 95 (FIG. 3) through the rear rocker leg 92 near the bottom thereof, to pivot the rocker 90 for rocking motion in a diametral plane (an upstanding diametral plane in FIGS. 3–6) of the body 41. The diametral through hole 66 provides plenty of front/rear space (FIG. 5) and sufficient transverse (FIG. 5A) clearance to allow free rocking of the rocker 90 about the axis of the pivot pin 94. In the embodiment shown, the bottom edge portion 96 of the rear leg 92 is narrowed transversely within the transversely necked in portion 67 of the diametral hole 66.

Integral wings 100 (FIGS. 3 and 6B) protrude transversely from the bight 91 and extend axially from the front leg 93 to a point about half way rearwardly along the length of the bight 91. The wings 100 overlie the upfacing blind holes 62. Coil springs 101 (FIGS. 3 and 6B) are located in respective ones of the blind holes 62 in the chordal flat 60 and extend upward therefrom into upward resiliently urging contact with the bottom of the wings 100, to urge the rocker 90 upward (in a clockwise direction in FIGS. 3–6), in pivoting relation around the axis of the pivot pin 94. The top (as seen in FIG. 3) of the bight 91 and wings 100 are convexly rounded to conform substantially to the concave interior of the cylindrical shell 50, so as to avoid unwanted contact therewith.

The depending front leg 93 is laterally wider than the rear leg 92, sufficiently so as to have a front/rear opening, vertically extended, generally oblong passage 102 (FIGS. 3, 4 and 6A) therethrough, for receiving the shank of the tool therethrough as hereafter described, while allowing rocking of the rocker 90 about the pivot pin 94 without interference of the top and bottom of the passage 102 with such a tool shank.

A locking pin 103 (FIGS. 3, 4 and 6A) extends transversely through the corresponding transverse hole 104 (FIG. 3) in the front leg 93 and is vertically located therein so that the transverse locking pin 103 extends across the bottom portion of the vertically elongate passage 102. The locking pin 103 preferably is freely rotatable within the rocker front leg 93, although it will function satisfactorily even if eventually made nonrotatable, as by corrosion. The locking pin 103 cannot escape transversely from its position in the front leg 93, because the ends of the locking pin 103 are trapped in clearance relation between the portions 105 (FIGS. 3 and 6A) of the body 41 flanking the rectangular diametral through hole 61. The locking pin 103 is provided with annular grooves 106 transversely just inboard of the body portions 105, and thereby just transversely within the passage 102, to accommodate the longitudinal edges of flats on a tool and avoid causing accidental burrs on such edges, as hereafter discussed.

The rocker 90 is capable of a range of pivotal movement about the axis of the pivot pin 94, such range including the radially outer and inner pivoted positions shown in FIGS. 4 and 5.

An axially inner portion of the hollow rotatable extension 35 is provided with a semi-circular (here about half a circle) relief 107 (FIGS. 6 and 4A) in its interior surface, which relief 107 extends axially into the diametral hole 62 in the body 41.

The present invention employs a special coupler 30 to transfer rotation from a motor shaft 23 to the chuck 12. More particularly, the rear portion of the coupler 30 has a rear opening recess 112 which receives and is fixed by any conventional means to the motor shaft 23. The reduced diameter front end portion of the coupler 30 defines the above mentioned rotatable shaft 13, which extends forward into the coaxial central opening 72 of the chuck body 41 (FIG. 6), wherein the set screw 71 axially slidably bears on a chordal flat 110 on the shaft 13 to allow the shaft 13 to rotatably drive the chuck 12.

The coupler 30 has an elongated coaxial bore 111 (FIG. 2) which extends from just behind the rotatable shaft 13 through the rear end of the coupler 30. The rear end portion of the bore 111 is radially expanded to form the abovementioned rear opening coaxial recess 112 in which the motor shaft 23 is fixedly received.

The axially intermediate portion 113 of the coupler 30 has a helical slot 118 cut therein, from the periphery thereof radially inward to the elongate bore 111. The helically formed intermediate portion 113 can thus act generally as a helical spring capable of some degree of circumferential twisting from end to end, and some degree of axial compression, so as to absorb circumferential and radial mechanical shocks, as might be encountered in use when a rotating tool driven thereby is pushed fast and hard against a bony surface at the surgical site. Thus, the coupler 30 helps, in use, to absorb mechanical shocks that might otherwise damage the tool, the chuck 12 or the motor 20. The coupler 30 is thus flexible, in the helically cut portion thereof, and so takes up any misalignment between the motor shaft 23 and the chuck body 41 and provides a higher torque carrying capability than would a rigid coupler of similar size. Couplers of this general type are known and are available from Helical Products located at Santa Maria, Calif. The particular flexible coupling 30 here shown is available under Stryker Corporation Part # 2296-300-17.

To assist in absorbing axial shocks, as well as to provide axial loading on the chuck bearings 44 and 45, the following structure is provided. A stop collar 114 (FIG. 2) is fixed by press fit inside the front end of the annular chuck housing 14, and positively blocks forward movement of the front bearing 44. The front part 16 of the motor housing 15 has telescoped slidably therewithin an elongate bearing loading shell 115.

A coil spring 116, backed by the motor housing front part 16, resiliently pushes forwardly the bearing loading shell 115 against the chuck rear bearing 45, which through the chuck body 41 pushes the front bearing 44 against the bearing stop collar 114 fixed in the front end of the chuck housing 14. The coil spring 116 (FIG. 2) helps reduce vibration and noise by in effect eliminating axial clearances at the front and rear chuck bearings 44 and 45 and helping to absorb (by compressing very slightly e.g. about .005 inch) a sudden axial load on the chuck 12, as when a tool chucked therein is thrust axially against the hard surface at a surgical site.

A generally conical nose cone 117 is fixed, by any convenient means not shown, on the frontmost portion of the hollow rotatable extension 35 and clears the stop collar 114. With the motor 20 turned off, the user can grip the nose cone 117 while inserting a tool into the chuck 12. In this way, the tool and chuck can be relatively angularly adjusted to seat the tool properly in the chuck, as hereafter more fully discussed.

Figure 7:
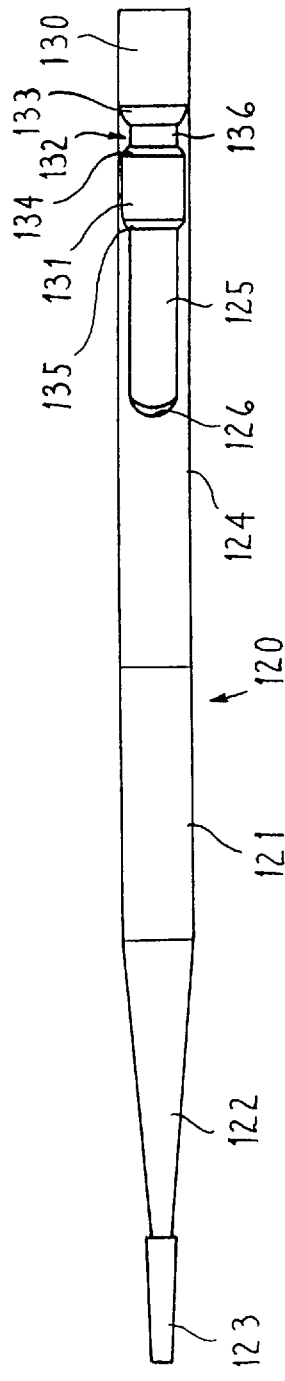
FIG. 7 is a view of a tool embodying the invention and of the type insertable in the FIG. 1 chuck, the FIG. 7 view being taken from the bottom side of the tool in the tool orientation shown in FIG. 4.
Figure 8:
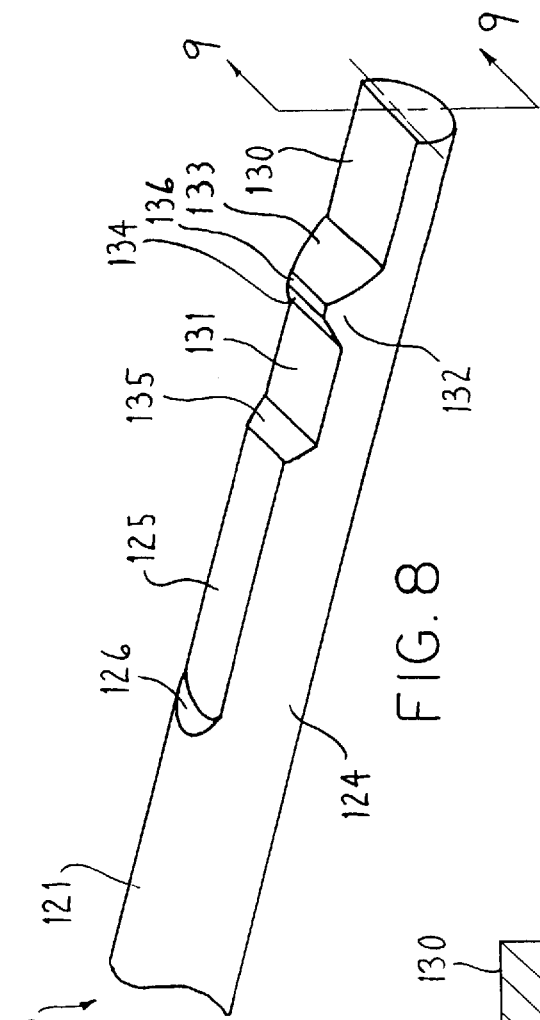
FIG. 8 is an enlarged fragmentary pictorial view of the chuck engaging shank of the FIGS. 4–7 tool.
Figure 9:
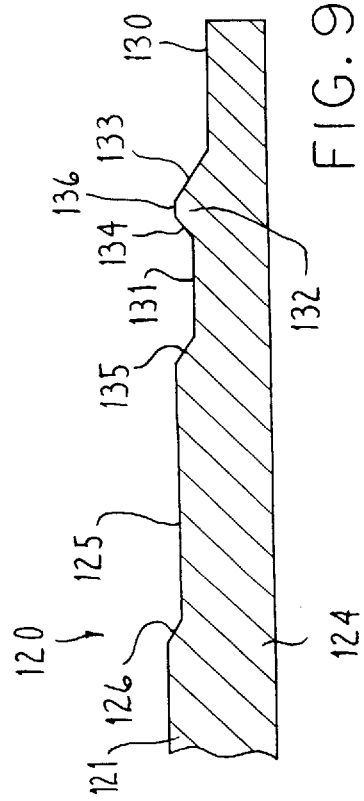
FIG. 9 is a central cross sectional view substantially taken on the line 9—9 of FIG. 8.

FIGS. 7–9 disclose a surgical tool 120 which comprises an elongate generally cylindrical shank 121. The shank 121, in the example shown in FIG. 7, includes a forward tapered nose 122 having a forwardly protruding material working tip 123, of any conventional kind, coaxially fixed on the front end thereof. Material working tips 123 of various shapes and kinds are known, in surgical tools of this general type, including burrs, drills, etc. The rear end portion 124 of the shank 121 includes a relatively shallow first flat 125. To the extent above described, the surgical tool 120 may be similar to prior art tools marketed by the assignee of the present invention, Stryker Corporation of Kalamazoo, Mich., for use with its prior art high speed handpiece (with included prior art chuck) above mentioned. An example of such prior art tool is Stryker Corporation Model No. 296-100-423.

Such a prior art tool is inserted into the mentioned prior art chuck as follows. The user first manually opens a spring loaded collet by twisting an unlocking collar while holding the handpiece housing with the other hand. The user's one hand then picks up the tool and pushes it into the chuck while rotating the tool into a proper circumferential alignment of the flat thereon with an internal drive member of the prior art chuck. The user's one hand is then shifted back to the locking collar to reverse rotate it back to its locked position, while holding the handpiece front end up, so the tool cannot fall out of such prior art chuck.

An objective of the present invention is to simplify the insertion and removal of such a high speed rotary surgical tool from chuck of such high speed rotary handpiece without jeopardizing the positive locking of the tool in the chuck during use.

Turning now to aspects of the tool more directly relating to the present invention, the tool shank 121 is provided with a relatively deep rear flat 130, extending forward from the rear end thereof and a middle flat 131 spaced forward from the rear flat 130 by a radially upstanding ramp member 132. The middle flat 131 is spaced rearward from the front end of the shallow flat 125. The flats 130, 131 and 125 are all chordal and define planes parallel to each other. The rear flat 130 is of depth equal to almost half the diameter of the shank 121. The ramp member 132 is formed by rear and front ramps 133 and 134. Other ramps 135 and 126 appear at the front of the flats 131 and 125 respectively. The peak 136 of the ramp member 132 is preferably at the same radial height as the front ramp 125.

In one tool constructed according to the present invention, a tool shank of about .922 inch diameter was about 0.051 inch thick at the rear flat 130, about 0.065 inch thick at middle flat 131 and about 0.080 inch thick at the radial top of the ramp member 132 and at the front flat 131. In that same tool constructed according to the invention, the rear flat was about .115 inch and the middle flat about 0.085 inch in axial length, the distance from the front of the middle flat to the rear end of the shank was about 0.276 inch while the distance from the front end of the front ramp 125 to the rear end of the shank was about 0.526 inch. The total length of tools constructed according to the invention may vary widely. Several units constructed according to the invention have been in the length range from 1.735 inch to 2.315 inch although greater and lesser lengths are contemplated. Further, it will be apparent that the tool and chuck can be sized upward and downwardly from those numbers given above by way of example.

The ramps 133, 134 and 135 angle up radially from there respective flats 130 and 131 preferably at an angle in the range of 30° to 40°, in one unit constructed according to the invention, at 35°.

The above discussed mounting structure at 130–135 can also be generally described as a rear and middle plateau 130 and 131 axially separated by a radially upstanding hill 132.

OPERATION

While the operation of the inventive apparatus will be apparent from the above description, same will be briefly summarized hereafter for convenient reference.

With the motor 20 deenergized, the tool 120 may be inserted into the chuck 12 as follows.

With no tool in the chuck, the springs 101 (FIG. 4) hold the rocker 90 radially outward against the interior of the shell 50. Preparatory to insertion of the tool, the operator holds the nose cone 117 and forward part of the chuck housing 15 in one hand and uses the other hand to rearwardly insert the shank 121 of a tool 120 into the open front end of the chuck hollow extension 35. When the rear end of the tool shank 121 encounters the locking pin 103, the user may have to partially rotate (to the extent of about 160° or less) the tool to cause the rear flat 130 to generally face and thereby clear the locking pin 103. When this occurs, the tool 120 moves further rearward easily until the rearward ramp 133 (FIG. 4) bumps into the locking pin 132. The flat 130, having cleared the locking pin 103, also clears the ledge 82 and overlaps the ledge 82 when the rear ramp 133 bumps into the locking pin 103.

As the relatively sharp side edges of the rear ramp 130 pass the locking pin 103, the rear ramp 130 may be cocked somewhat with respect to the locking pin 103. If so, one of the side edges of the rear flat 130 might bear on a purely cylindrical locking pin. However, such side edge of such rear flat 130, rather than bearing on the outer surface of the locking pin 103, will instead be received gently, with some clearance, in one of the annular grooves 106 of the locking pin 103, so as to avoid any tendency to flatten or burr the edge of the tool flat 130. This avoids the possibility of difficulty in removing a tool from the chuck due to effective tool radius increase at a radially outward burr on such a side edge.

When the rear facing tool ramp 133 encounters the locking pin 103, the user receives a tactile cue in the form of a slightly increased resistance to the rearward insertion of the tool shank 121 into the chuck.

The user applies only a relatively small force rearward on the tool, sufficient to cause its rear ramp 133 to press the locking pin 103 aside (downward in the transition from FIG. 4 to FIG. 5). This pivots the rocker 90 counterclockwise about the pivot pin 94 and against the springs 101, from its FIG. 4 position to its FIG. 5 position.

Further rearward pressure on the tool by the user snaps the hill 132 past the locking pin 103 and carries the tool substantially instantly to its fully rearward, fully installed FIG. 6 position. The force required to transition from FIG. 5 to FIG. 6 is reduced compared to the force required to transition from the FIG. 4 to FIG. 5, since the locking pin moves off the peak of the 132, down the front ramp and onto the middle flat 131, assisted by the springs 101. The springs 101 thus pivot the rocker 90 counterclockwise to an intermediate position, namely, a position between the FIG. 4 and FIG. 5 positions, so as to positively grip the tool shank.

Rearward movement of the tool shank 121 is positively stopped by collision with the abutment face 84 of the abutment plug 81. Thus, the user receives a tactile cue when the tool 120 moves off the hill 132 past the locking pin, to snap into its fully installed position abutting the abutment plug 81. This transition from FIG. 5 to FIG. 6 provides a clear tactile cue to the user that the tool 120 is now fully installed. Normally, the user will receive an auditory cue in the form of a click as the rear end of the tool 120 hits the abutment plug 81.

Further, the rearwardmost position of the tool 120 is preferably such that the locking pin 103 is spaced slightly in front of the hill 132 so that the user can obtain a further tactile cue, as to the fully installed condition of the tool in the chuck, by being able to jiggle the tool slightly forward and rearward with respect to the chuck, namely between abutment of the rear end of the tool against the abutment plug 81 and abutment of the front ramp of the hill 132 against the locking pin 103.

Upon activation of the handpiece motor 120, the chuck and installed tool 120 begin rotation and quickly reach normal operating speed (for example 85,000 rpm or 100,000 rpm in the examples discussed above). As rotational speed increases, centrifugal force on the center of mass of the rocker 90 (which center of mass is located above the tool 120 in FIGS. 5–6) presses the locking pin 103 harder and harder up against the tool middle flat 131. The resulting upward force on the middle flat 131 presses the upper portion of the tool shank 120 harder and harder up against the upper interior surface of the bore 72.

Thus, centrifugal force on the rocker 90, due to such rotation, applies a much stronger clockwise (FIG. 6) force on the rocker 90 than accomplished by springs 101 at rest and hence, the locking pin 103 is pressed much harder against the flat 131 to press the upper side of the tool shank 121 very hard against the upper (in FIG. 6) side of the coaxial central opening 72 forward of the rocker 90. This prevents the rotating tool 120 from escaping forward from its fully installed position in the chuck 12. For example, in one unit constructed according to the invention, with the motor deenergized, the force required to push a tool 120 fully into the chuck 12 was about 3 pounds and the force required to manually pull such tool 120 from the chuck 12 was about 1 pound. On the other hand, with the motor energized and the chuck and tool rotating at, for example, 85,000 rpm to 100,000 rpm the force required to pull the rotating tool 120 forwardly out of the rotating chuck 12 increases dramatically, to something in the range of 20 to 35 pounds.

To achieve this effect, the rocker is carefully configured and located within the chuck body. More particularly, the pivot pin 94, in the preferred embodiment shown, (with the locking pin 103) is located below (in FIG. 6) the rotative axis of the chuck and tool whereas the bight 91 of the rocker 90 and springs 101 are located on the opposite side of the rotational axis (above the rotational axis in FIG. 6). In any event, the apparatus is arranged so that the center of mass of the rocker 90 and springs 101 is on the opposite side of the rotative axis from the locking pin 103, to provide a resultant radial force, during rotation, directed to push the locking pin 103 hard against the opposed middle flat 131 of the tool.

Accordingly, the rotating chuck 12 provides a very strong grip on the tool 120 and, acting against any tendency of the tool 120 to move forward out of the chuck, a forcible gripping much stronger than the relatively light force required to install or remove the tool 120 in the nonrotating chuck.

In addition to the tactile cues above discussed, by which the user can be assured that the tool is fully inserted into and gripped by the chuck, the tool shank 121 also is preferably marked with a conventional annular guideline 140 which is visible to the user before the tool 120 is fully inserted into the chuck 12 (as in FIG. 5), but which enters the hollow shaft extension 35 just far enough to become hidden therein when the tool 120 is fully axially inserted into the chuck as in FIG. 6.

Note in FIG. 4 that the surrounding sleeve 50 positively sharply limits the clockwise limit of rotation of the rocker 90 that can be achieved with no tool loaded in the chuck. Thus, should the electric motor be turned on with no tool in the chuck, the rocker 90 has its center of mass not much further off the rotational axis than it would be with a tool fully installed in the chuck as in FIG. 6. As a result, running the motor with the chuck empty does not lead to severe eccentricity or out of balance conditions within the chuck. Indeed, the range of normal movement of the rocker between its FIG. 5 outward and FIG. 6 tool chucked positions, is relatively small.

The tool 120 can easily be removed from the chuck 12, after the rotation of the chuck has stopped, simply by lightly pulling the tool 120 in a forward direction, whereupon the tool is pulled forward out of the chuck, in a reversal of the steps above discussed for chucking of the tool in the chuck. The force retaining the tool 120 in the nonrotating chuck 12, is just great enough that if the user grips the tool but lets go of the handpiece, the grip of the chuck on the tool is sufficient to support the static weight of the handpiece.

The chuck 12 is structured so that, with a tool chucked therein as in FIG. 6, the chuck 12 is substantially in static and dynamic balance. Applicant recognizes the importance of accurate balancing of the rotating chuck 12 in view of the very high speed (e.g. 100,000 rpm) of rotation of the chuck 12 in use. Accordingly, after assembly, each chuck 12 is preferably spun up to a suitable speed on a test bench noting any imbalance, and obtaining more accurate balance by milling away a small portion of the outer surface of the sleeve 50 in the appropriate circumferential portion of the front or rear quarter of its length. In this way, minor imbalance that might be occasioned, e.g. by stacking of internal machining tolerances, one way or another, can be compensated.

Although the chuck 12 is preferably constructed of substantially non-corrodible material (for example of stainless steel), it is possible that the front portion of the central opening 72 (FIG. 4) where the tool 120 is to be inserted, may suffer slow corrosion over the life of the handpiece. Although the radial clearance between the outer periphery of the tool 120 and the wall of the central opening 72 is kept very small (for example about 0.0005 inch) to avoid any tendency of the tool 120 to wobble or become eccentric in the chuck at high rotational speeds, in general corrosion of the internal bore of the hole 72 has not been a problem. It is hypothesized that once the tool 120 is fully chucked, as in FIG. 6, normal high speed rotation and use of the apparatus may set up relative micro motion between the periphery of the shank of the tool 120 and the opposed interior wall of the coaxial bore 72 to polish off any corrosion as it develops. On the other hand, the circumferential portion of the bore 72 that opposes the flats 130, 131 on the shank of the tool 120 does not come in contact with the tool shank during rotation, so that there can be no such removal polishing off of corrosion from that part of the interior surface of the bore 72. Accordingly, it is contemplated that corrosion might in time build up on that part of the interior surface of the bore 72, and as a result of a very small radial clearance between the tool and the interior surface of the bore 72, that pushing of the tool into the bore 72 and rotation of the tool into proper alignment of its flats with the locking pin 103 might be impeded by such a long term build-up of corrosion.

This problem is solved by the present invention by providing the shallow axial and circumferential relief 107 in the portion of the bore 72 which normally faces the flats 125 and 131 on the tool during normal operation of the handpiece. Providing the relief 107 as shallow as 0.005 inch would allow substantial corrosion to grow over time on relief 107 and still leave its corroded surface spaced radially outward beyond the remainder of the interior surface of the bore 72 and hence clear of contact with the shank of the tool 120 even as the rear end of the tool shank slides axially rearward past the relief 107 with the rounded, rather than flatted portion of the tool shank adjacent the corrosion relief 107 (prior to proper angular opposition of the tool rear flat 130 to the locking pin 103, i.e. to face downward in FIG. 4).

During the development of the present invention, it was found that several improvements could be made over the prior high speed surgical apparatus of the present assignee.

First, the present invention simplifies the chucking unit and unchucking of the tool. In the prior apparatus, to chuck a tool, one hand of the user gripped the handpiece and the second hand of the user first twisted a locking collar on the handpiece to a collet unlocked position, the second hand then shifted to pick up the tool and insert it into the chuck, and the second hand then shifted back to the locking collar, to reverse twist it back to its collet locked position, the user in the meantime taking care to keep the forward end of the handpiece aimed upward so as not to allow the tool to fall out of the chuck by gravity prior to twisting of the locking collar back to its locked position. Removal of the tool from the prior chuck required a reversal of these steps.

In contrast, in the present invention the first hand of the user can simultaneously grip the nose cone 117 and chuck housing 14 while the second hand of the user simply inserts the tool into the chuck. Removal of the tool from the chuck is by a reversal of these steps. Thus, there is no need for the user to shift his second hand from one object to another during loading and unloading of the tool in the chuck.

Further, the present invention substantially reduces the possibility of liquid from the surgical site leaking into and damaging the chuck bearings. In the prior apparatus above discussed, the locking collar was located centrally along the length of the chuck and protruded through the chuck housing so as to be manually rotatable for locking and unlocking the chuck. This left a question of risk of leakage of liquid from the surgical site into the chuck through clearances between the locking collar and the front and rear portions of the chuck housing. Further, there was a question of risk of liquid leakage into the chuck along the tool and along the outside of the front portion of the rotatable shaft of the chuck, from both of which paths liquid had access to the chuck bearings.

In contrast, the present invention eliminates the locking collar and provides no radially inward entry for liquid through the chuck housing, at any location along the length of the chuck. In addition, any liquid leaking along the tool shank 121 and through the central opening 72 of the chuck into the interior of the chuck body, cannot reach the bearings 44 and 45 because of the tight, sealed connection of the surrounding shell 50 at its front and rear ends along the annular ribs 46 and 47 of the chuck body. Further, any liquid attempting to leak radially inwardly between the nose cone 17 and the stop collar 114 (FIG. 2), during rotation, is thrown radially outward by centrifugal force due to rotation of the nose cone 117 with the chuck 12, the narrow axial clearance between the nose cone 117 and the annular stop collar 114, so that such liquid never reaches the radial clearance between the rotating shaft and the interior of the stop collar 114. A unit built according to the present invention, with a tool 120 chucked therein, was run at full rotational speed with the front portion of the chuck housing 14 immersed in a bucket of water. After removal from the bucket of water, the unit was dismantled and no water was found in the bearings.

Further, the mentioned prior chuck did not have preloaded bearings. It was found that different units of the prior art chuck would tend to be noisy in operation and the loudness and character of the noise would vary from unit to unit. The present invention, with its spring 116 (FIG. 2) loading the chuck bearings 144 and 145, tends to be much quieter and the level and quality of bearing noise is more consistent from unit to unit, thereby reducing user annoyance and any tendency of the user to assume that bearing failure is going to occur even when it was not. Similarly, bearing manufacturers generally recommend that the bearings be loaded with an optimal force for maximum life span and the present invention has its preload spring 116 selected to approach optimal preloading for maximum bearing life. In addition, the resilient preloading of the chuck bearings 44 and 45 by the spring 116 provides some protection from axial shock loading if the user bumps the working end of the rotating tool axially against a hard surface, such as any bony layer, as above discussed.

The tool 120 (FIGS. 7–9) embodying the present invention is usable not only with the inventive chuck (FIGS. 1–6), but also with the above mentioned prior chuck. This allows owners of that prior chuck to continue using same as long as it is serviceable and to do so with new tools 120. This relieves such prior users and the manufacturer and suppliers of the handpieces and tools embodying the present invention from having to maintain an inventory of the prior art tools.

At the same time, the inventive chuck of FIGS. 1–6 will not grip the mentioned prior tool. To prevent a user from attempting, through error, to chuck the prior tool in the inventive chuck 12, the prior tool is difficult to insert past the locking pin 103 because the shallow flat 125 runs all the way to the rear end of the tool. Moreover, even if the rear end of the prior tool is pushed past the locking pin 103, it bottoms against the front end of the ledge 82 of the abutment plug 81, which positively precludes full insertion of the prior art type tool into the inventive chuck 12. As a result, the annular guideline 140 on the prior tool can never be brought axially rearward anywhere near the front end of the chuck extension 35 and so gives clear visual warning that the tool is not chucked in the chuck 12. Further, the tactile cues, which the user receives upon pushing the hill 132 of an inventive tool 120 past the locking pin 103, are never given when the user attempts to chuck such prior tool in the inventive chuck 121.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A replaceable rotary patient tissue working tool and a high speed rotational surgical handpiece having a centrifugal chuck for axial push-in chucking and pull-out release of such a tool, comprising in combination:

a chuck comprising an axially extending drive shaft having a rotatably driveable rear end portion and having a hollow front end portion comprising a central passage for receiving a rear shank of a tissue working tool to be rotatably driven, a centrifugal locking member with a mass portion located on one side of a rotational axis of said drive shaft, said centrifugal locking member being pivoted on an axis transverse to said drive shaft axis, a front leg extending radially past said central passage from said mass portion, said front leg having tool gripping means on the opposite side of said central passage for receiving a tool rear shank rearward axially therepast and for more strongly radially gripping such tool shank in response to faster rotation of said drive shaft, and to resulting increasing centrifugal radial outward force on said mass portion;

a tool comprising an elongate rear shank, patient tissue working means at a front end portion of said shank, mounting means at a rear end portion of said shank, said mounting means comprising a rear plateau relieved in one side of said shank and extending to the rear end of said shank, a hill protruding radially from said rear plateau and extending forward along said shank therefrom, a second plateau radially depressed from said hill and extending forward therefrom along said shank, said mounting means being receivable in said chuck with said tool second plateau radially opposed by said gripping means of said chuck and with said hill located rearward in said chuck beyond said gripping means for preventing unintended forward movement of said tool with respect to said chuck and said rear plateau of said tool extending further rearward into said chuck and being rearward spaced from said gripping means of said chuck by said hill, said tool extending forward through said hollow front end portion of said drive shaft toward said tissue working means, said tissue working means being exposed in spaced relation ahead of said chuck.

2. The apparatus of claim 1 in which said plateaus are flats in parallel planes chordal to said tool shank, said gripping means comprising a locking pin extending transversely to said rotational axis and carried on said front leg.

3. The apparatus of 2 in which said flats have relatively sharp longitudinal edges, said locking pin having laterally spaced annular grooves for receiving a said longitudinal edge during partial rotation of said tool shank as said tool shank is guided passed said locking pin into said chuck.

4. The apparatus of claim 1 including an abutment member closing a rear end portion of said central passage and having a chordal ledge extending forward toward said gripping means for blocking insertion therepast of a non-intended tool, said chordal ledge and said rear plateau being radially opposable to allow insertion of the rear portion of said tool shank rearward past said chordal ledge and thereby for allowing insertion therepast into said chuck of an intended tool.

* * * * *

UNITED STATES PATENT AND TRADEMARK OFFICE
CERTIFICATE OF CORRECTION

PATENT NO. : 5 833 704
DATED : November 10, 1998
INVENTOR(S) : Daniel L. McCombs et al It is certified that error appears in the above-identified patent and that said Letters Patent is hereby corrected as shown below:

In the Title; change "THEREFORE" to ---THEREFOR---.

In the Abstract, line 4;
    change "includes" to ---comprises---.

Column 14, line 13; before "2" insert ---claim---.
    line 17; change "passed" to ---past---.

Signed and Sealed this

Fourth Day of April, 2000

Attest:

Attesting Officer

Q. TODD DICKINSON

Director of Patents and Trademarks